US 8,665,448 B2

(12) United States Patent
Heidrich et al.

(10) Patent No.: US 8,665,448 B2
(45) Date of Patent: Mar. 4, 2014

(54) SENSOR ARRANGEMENT AND DETECTION METHOD

(75) Inventors: Helmut Heidrich, Berlin (DE); Peter Luetzow, Berlin (DE)

(73) Assignee: Fraunhofer-Gesellschaft zur Förderung der angewandten Forschung e.V. (DE)

( * ) Notice: Subject to any disclaimer, the term of this patent is extended or adjusted under 35 U.S.C. 154(b) by 48 days.

(21) Appl. No.: 13/202,206

(22) PCT Filed: Jan. 8, 2010

(86) PCT No.: PCT/EP2010/000184
§ 371 (c)(1),
(2), (4) Date: Oct. 28, 2011

(87) PCT Pub. No.: WO2010/105716
PCT Pub. Date: Sep. 23, 2010

(65) Prior Publication Data
US 2012/0057173 A1    Mar. 8, 2012

(30) Foreign Application Priority Data
Mar. 16, 2009 (DE) .................. 10 2009 013 878

(51) Int. Cl.
*G01B 9/02* (2006.01)
*G01D 5/353* (2006.01)
(52) U.S. Cl.
USPC .............................. 356/477; 356/493; 385/13
(58) Field of Classification Search
USPC ........... 356/47, 504, 481, 517, 491, 492–495; 385/8, 13
See application file for complete search history.

(56) References Cited

U.S. PATENT DOCUMENTS 4,179,189 A * 12/1979 Kaminow et al. ............. 385/128
4,886,361 A    12/1989 Furstenau
(Continued)

FOREIGN PATENT DOCUMENTS

| DE | 4138222 | 12/1992 |
| DE | 19931754 | 2/2000 |
| WO | WO-97/37197 A1 | 10/1997 |
| WO | WO-2006/127034 A2 | 11/2006 |

OTHER PUBLICATIONS

Albrecht.TE/TM Mode Splitters on InGaAsP/InP.2. Feb. 1990,IEEE Photonics Technology L.etters, vol. 2. No. 2.*

(Continued)

*Primary Examiner* — Michael A Lyons
*Assistant Examiner* — Maurice Smith
(74) *Attorney, Agent, or Firm* — Schwegman Lundberg & Woessner, P.A.

(57) ABSTRACT

The invention relates to an optical sensor arrangement comprising a measuring optical fiber demonstrating birefringence modifiable as a function of a measurement variable, and to an optical analysis unit having two optical branches implemented as optical fibers forming a Mach-Zehnder interferometer and an optical coupler for bringing together light guided in the two branches, wherein at least one output of the coupler is optically connected to at least one light-sensitive element, and wherein the analysis unit comprises a polarizing beam splitter from which the optical branches originate, wherein the measurement optical fiber is connected upstream of an optical input of the polarizing beam splitter, and wherein a polarization converter is disposed in a course of one of the optical branches. The invention further relates to a detection method that can be performed using said sensor arrangement.

14 Claims, 2 Drawing Sheets

(56) References Cited

U.S. PATENT DOCUMENTS

Figure 1:
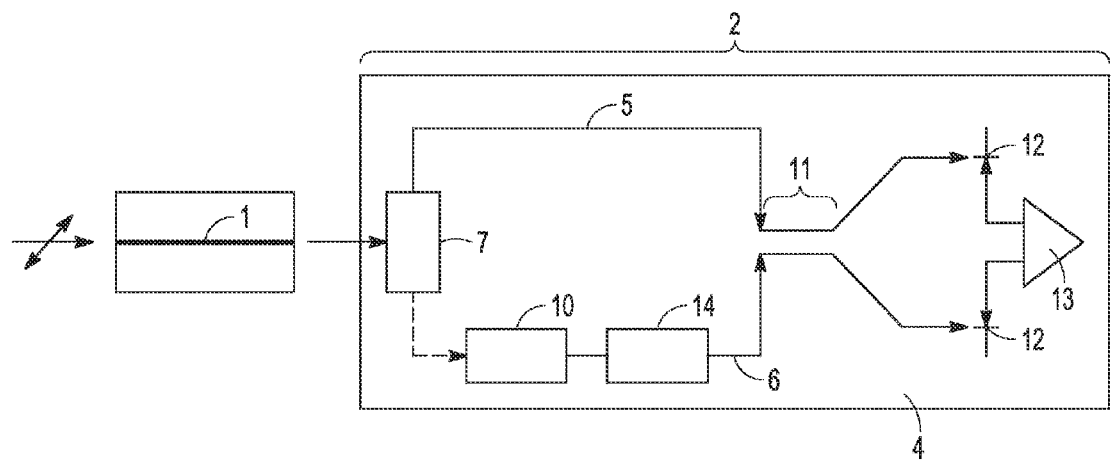

| | | | | |
|---|---|---|---|---|
| 5,199,097 | A | * | 3/1993 | Shinokura et al. ............. 385/122 |
| 5,420,688 | A | * | 5/1995 | Farah ............................. 356/477 |
| 5,708,734 | A | * | 1/1998 | Van Der Tol .................... 385/11 |
| 6,137,576 | A | | 10/2000 | Pauluth et al. |
| 6,493,090 | B1 | * | 12/2002 | Lading et al. .................. 356/484 |
| 6,813,398 | B1 | * | 11/2004 | Taylor et al. .................... 385/11 |
| 7,505,640 | B2 | * | 3/2009 | Little .............................. 385/11 |
| 2004/0239944 | A1 | * | 12/2004 | Shirai et al. .................... 356/481 |
| 2006/0204197 | A1 | * | 9/2006 | Miyadera et al. ............. 385/129 |

OTHER PUBLICATIONS

Albrecht Klotz, Andreas Brecht Channel waveguide mode beat interferometerA. Sensors and Actuators B 38-39 (1997).*

J. J. G. M. van der Tol, "Realization of a Short Integrated Optic Passive Polarization Converter", Aug. 8, 1995.*

"Internatonal Application No. PCT/EP2010/000184, International Preliminary Report on Patentability issued Sep. 20, 2011", (w/ English Translation of Written Opinion), 10 pgs.

"International Application No. PCT/EP2010/000184, International Search Report and Written Opinion mailed Apr. 23, 2010", 17 pgs.

Albrecht, P., et al., "TE/TM Mode Splitters on InGaAsP/InP", IEEE Photonics Technology Letters, Vo. 2, No. 2, (Feb. 1, 1990), 114-115.

Borisov, S. M., et al., "Optical Biosensors", Chem. Rev., 108(2), (2008), 423-461.

Fattinger, CH., et al., "The different interferometer: a highly sensitive optical probe for quantification of molecular surface concentration", Biosensors and Bioelectronics, vol. 8, (Jan. 1, 1993), 99-107.

Heidrich, H., et al., "Passive Mode Converter with a Periodically Tilted InP/GaInAsP Rib Waveguide", IEEE Photonics Technology Letters, Vo. 4, No. 1, (Jan. 1, 1992), 34-36.

Klotz, Albrecht, et al., "Channel waveguide mode beat interferometer", Sensors and Actuators B 38-39, vol. 39, No. 1-3, (Mar. 1, 1997), 310-315.

Koster, Ton, et al., "Fully integrated optical polarimeter", Sensors and Actuators B, vol. 82, No. 2-3, (Feb. 28, 2002), 213-226.

Lukosz, W., et al., "Difference interferometer with new phase-measurement method as integrated-optical refractometer, humidity sensor and biosensor", Sensors and Actuators B, vol. 39, No. 1-3, (Mar. 1, 1997), 316-323.

* cited by examiner

SENSOR ARRANGEMENT AND DETECTION METHOD

PRIORITY CLAIM TO RELATED APPLICATIONS

This application is a national stage application under 35 U.S.C. §371 of PCT/EP2010/000184, filed Jan. 8, 2010, and published as WO 2010/105716 A1 on Sep. 23, 2010, which claims priority to German Application No. 10 2009 013 878.1, filed Mar. 16, 2009, which applications and publication are incorporated herein by reference and made a part hereof in their entirety, and the benefit of priority of each of which is claimed herein.

The invention relates to an optical sensor arrangement according to the preamble of the main claim, as well as to a detection method which may be carried out with such a sensor arrangement and with which the presence of a concentration of a substance or a mechanical loading may be detected.

A sensor arrangement of the known type comprises a measurement waveguide which displays a double refraction which changes in dependence on a measured variable, as well as an optical evaluation unit with two optical arms which are realised by waveguides and which form a Mach-Zehnder interferometer, and with an optical coupler for leading together light which is led in the two arms, wherein at least one output of the coupler is optically connected to at least one light-sensitive element. Thereby, very generally, an optical arrangement which has two different optical paths which depart from a beam splitter and are led together again for the at least partial superposition, is to be understood as a Mach-Zehnder interferometer in the present document.

A sensor of this type which is known from the state of the art is described in the document DE 41 38 222 C1. Here, it is suggested to measure a phase shift which occurs under the influence of a variable to be measured, within the Mach-Zehnder interferometer realised as integrated optics. A sensitive region of this sensor may therefore not be arranged in a manner which is spatially separated from the integrated optics which also contain electrical components, which is why an application of the sensor is not possible in an environment which reacts sensitively to electricity. Since the sensitive region is arranged within a path of the Mach-Zehnder interferometer, strict limits are again placed on its spatial extension, which thus also disadvantageously limits a sensitivity of the sensor.

It is therefore the object of the invention to provide a comparable sensor arrangement which avoids these disadvantages and permits the realisation of measurement sensitivities which may be adapted to different tasks and which are particularly high, wherein an application is also to be possible in environments which are critical with regard to electric fields or electrical conductors. It is also the object of the invention to suggest a corresponding advantageous method for detecting a substance or a mechanical loading.

According to the invention, this object is achieved by a sensor arrangement with the characterising features of the main claim in combination with the features of the preamble of the main claim, as well as by a detection method with the features of claim 14. Advantageous designs and further developments of the invention are to be deduced from the features of the dependent claims.

Due to the fact that the evaluation unit comprises a polarising beam splitter, from which the mentioned optical arms depart, wherein the measurement waveguide is arranged in front of an optical input of the polarising beam splitter and wherein a polarisation converter is arranged in a course of one of the optical arms, a phase shift between the polarisation shares of a light bundle which occurs within the measurement waveguide, may be detected in a manner spatially separated therefrom by the Mach-Zehnder interferometer. Thereby, a mode splitter, with which typically two basic eigenmodes of two polarisations which are orthogonal to one another are separated, is indicated as a beam splitter, wherein an input and two outputs of the mode splitter are formed by waveguides, thus the beam splitter is not to be designed as a free beam arrangement. The suggested measures thus advantageously permit an arrangement of the measurement waveguide in a manner which is separated spatially from the evaluation unit and thus also from all electrical components, said measurement waveguide e.g. being able to be connected to the evaluation unit by way of a polarisation-maintaining waveguide. The waveguide may also be designed in a largely infinite manner and in particular with an infinite length, by which means in each case suitable and in particularly also very high sensitivities of the sensor arrangement may be realised for different applications.

The polarising beam splitter which is designed for feeding light shares of different polarisation into the two arms, is typically designed as a so-called TE/TM splitter, thus in a manner such that it breaks down a fed-in light bundle into two components which are linearly polarised orthogonally to one another, of which one is TE-polarised and one is TM-polarised. Accordingly, the polarisation converter may be designed as a TE/TM converter.

A correspondingly advantageous detection method which, depending on the design of the measurement waveguide, may be used for detecting a presence or a concentration of a substance as well as for detecting a mechanical loading and which may be carried out with a sensor arrangement of the type described here, envisages light with two orthogonal polarisation shares being fed into a measurement waveguide which for these polarisations displays a double refraction changing in dependence on an accumulation of the substance and/or the mechanical loading, thus different indices of refraction for these shares—e.g. by way of feeding in light with a linear polarisation which is inclined by 45° with respect to main axes of the measurement waveguide. After leaving the measurement waveguide, the two shares are separated and are led through two different optical arms, where the polarisation of at least one of these shares is changed, and specifically such that light with components of the same polarisation exits at an output of this arm and of the other aim. The two shares are finally superimposed again at an output of the two arms, wherein a phase shift between the two shares is detected by way of intensity measurement of a superposition of the two components. A superposition of the two shares is thereby possible by way of changing the polarisation in at least one of the arms, for which the polarisation converter of the suggested sensor arrangement is provided.

In order to permit such a detection method, the suggested sensor arrangement preferably further comprises a linearly polarised, monochromatic laser light source for feeding polarised light into the measurement waveguide, said source being designed and arranged such that the light fed into the measurement waveguide contains shares of two polarisations which are of such a difference, that in each case one of these shares is led through the beam splitter in each of the two arms of the evaluation unit. Moreover, the measurement waveguide and the beam splitter are preferably orientated to one another such that two light shares which are led through the beam splitter into the different arms are polarised such that these light shares in the measurement waveguide propagate in each case with a defined—even if dependent in each case on the measured variable—refractive index, thus in each case are typically polarised in a linear manner parallel to an optical main axis of the measurement waveguide. Both shares should be fed in with an as equal as possible intensity which e.g. may be achieved by way of feeding in the light with a linear polarisation which is inclined by 45° with respect to the main axes of the measurement waveguide.

An advantageously compact and robust construction of the sensor arrangement results if at least the evaluation unit is designed as integrated optics, with which the beam splitter, the optical arms with the polarisation converter, and the coupler, possibly also the at least one light-sensitive element, are arranged on a common planar substrate, from which they are typically separated by way of an optical buffer. This substrate may e.g. be formed of a part of a wafer and for example of silicon or lithium niobate, wherein the evaluation unit may also be manufactured on the wafer plane, thus before the separation of the wafer into numerous chips. A manufacture with SOI-technology is particularly possible. Cores of the waveguides may be realised e.g. by ribs above the substrate or the buffer. In this case, a light wave with an electrical field orientated parallel to the substrate maybe indicated as TE-polarised, and a light wave with a magnetic field orientated parallel to the substrate may be indicated as TM-polarised.

If the sensor arrangement is to be suitable for detecting a substance, the measurement waveguide may carry a selective layer for accumulating this substance. Thus the sensor arrangement may in particular be designed as a bio-sensor. Suitable materials for the selective layer have been known for some time, and the e.g. the article "Optical Biosensors" by S. M. Borsiov and O. T. Wolfbeis, Chem. Rev. 2008, 108, 423-461 is referred to. The accumulation of the substance should thereby have a polarisation-dependent influence on light transported in the measurement waveguide, which is why the selective layer is not to be deposited on all sides and preferably only one an upper side of the measurement waveguide.

Alternatively or additionally, the sensor arrangement may also be designed for detecting a mechanical load. So that this has an influence on a double refraction of the measurement waveguide, this measurement waveguide for this may be designed a freely floating manner at least in sections, i.e. as a cantilever, for which a sublayer of the measurement waveguide maybe etched away at locations.

On account of a core of the measurement waveguide being of an optically single-axis material, such as e.g. lithium niobate, one may succeed in this being double-refractive also in an initial condition, in which it is not occupied with the substance to be detected or is not loaded. Alternatively or additionally, the measurement waveguide for this purpose may also have an anisotropic cross section, e.g. with a design as a rib waveguide on a planar substrate and possibly additionally subjected to a mechanical bias. A particularity high measurement sensitivity results thereby when the measurement waveguide is double-refractive also in the non-loaded or non-occupied condition and has a length which corresponds to several beat lengths between light shares of a different polarisation. Thereby, the length of a section along which a relative phase shift of exactly $2\pi$ results between the light shares of the two polarisations is thereby indicated at the beat length.

It is particularly advantageous if the measurement waveguide is designed in a single-mode manner, thus such that it permits only in each case one mode to propage for each of the two polarisations. Dispersions between different modes of the same polarisation may be avoided by way of this, which in turn renders possible a high sensitivity. For the same reason, it is advantageous if the waveguide forming the arms of the evaluation unit and preferably all waveguides of the sensor arrangement at least in sections are designed in a single-mode manner. In any case, all waveguides of the sensor arrangement should be as polarisation-maintaining as possible, with the exception of the polarisation converter.

At least one of the optical arms of the evaluation unit may also comprise a phase shifter. This may be realised e.g. by way of utilisation of a dependency between the refractive index of a waveguide core and an electrical field which prevails there and which in turn may be adjustable by way of a control voltage which may be applied to electrodes in an environment of the waveguide core.

The polarising beam splitter may be realised with regard to design in a simple manner in the form of a directional coupler with two waveguide sections which run parallel to one another along a coupling section, wherein these waveguide sections may have different cross sections, in order to favourise light of a different polarisation Alternatively or additionally, also one of these waveguide sections on one side—e.g. at the top—may carry a metallic coating, by way of which the TM-polarised light shares are suppressed. Alternatively, the beam splitter may also be designed as a Y-splitter with outputs of different cross sections or as multimode interference couplers (MMI).

The optical coupler may in turn be given by an optical four-point network and typically be designed likewise as a directional coupler. A reliable detection of a relative phase shift between light shares which originally had different polarisations is then possible by way of each of two outputs of the coupler being connected in each case to a light-sensitive element. Electrical outputs of these light-sensitive elements for this may be connected to inputs of a differential amplifier.

The polarisation converter may be designed in a passive manner, thus without electrodes and for this e.g. be given by a waveguide with a cross-sectional shape which changes along a course of a waveguide. This too contributes to a simple construction and to a low proneness to malfunctioning.

Finally, the sensor arrangement may also comprise several measurement waveguides which are optically connected to the input of the beam splitter or may be selectively connected to the beam splitter, e.g. by way of optical switches. Then a single evaluation unit is sufficient for reading out many sensors which in each case may be given by a suitably designed waveguide and therefore may themselves be constructed in a simple manner. Thereby, the different measurement waveguides may be arranged at different locations and/or be sensitive to different sensors or measured variables.

Figure 2:
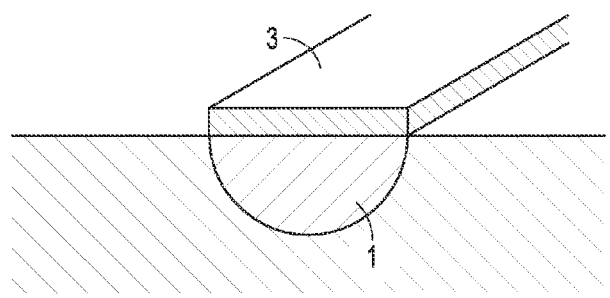
Figure 3:
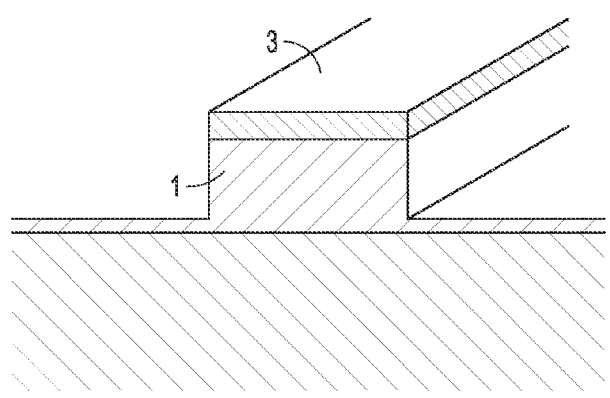
Figure 4:
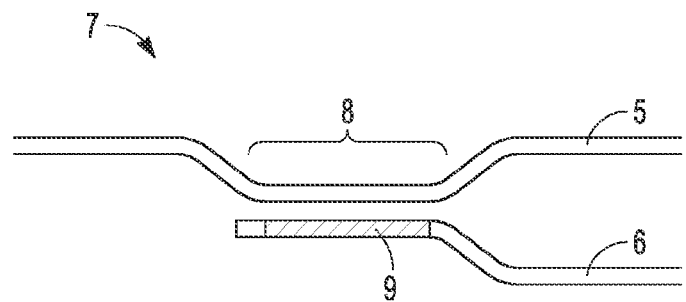
Figure 5:
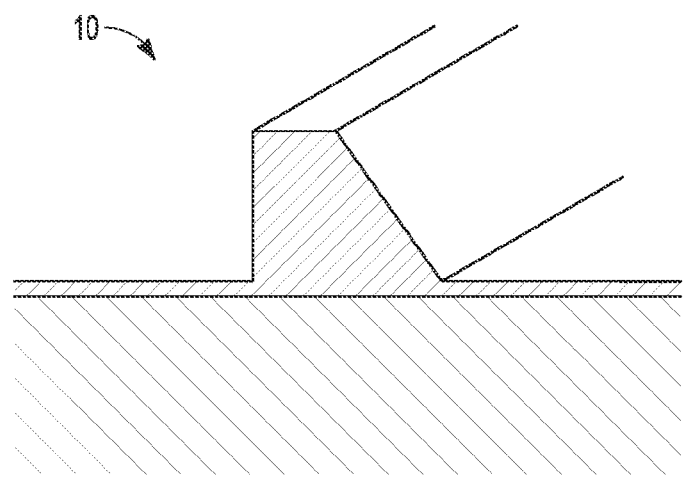

Embodiment examples of the invention are described hereinafter by way of the FIGS. 1 to 4. There are shown in:

FIG. 1 a schematic representation of an optical sensor arrangement,

FIG. 2 a perspectively represented detail of a measurement waveguide of the sensor arrangement of FIG. 1 with a cross section of this measurement waveguide, FIG. 3 in a representation according to FIG. 2, a measurement waveguide for a modification of this sensor arrangement, FIG. 4 a plan view of a polarising beam splitter of the sensor arrangement shown in FIG. 1, FIG. 5 a perspectively represented detail of a waveguide which forms a polarisation converter from this sensor arrangement, wherein in particular a cross section of this waveguide is to be recognised.

A schematised view of an optical sensor arrangement is shown in FIG. 1, and may be applied as a biosensor and is suitable for detecting a concentration of a certain substance.

In a modification, this sensor arrangement is also suitable for detecting a mechanical loading. The shown sensor arrangement comprises a measurement waveguide 1 and an optical evaluation unit 2 which is arranged spatially separated from the measurement waveguide 1 and is optically connected to this by a polarisation-maintaining waveguide.

The measurement waveguide 1, of which a section is shown in FIG. 2, is designed in a single-mode and double-refractive manner and has a double refraction which changes depending on a measured variable. Thereby, the concentration of the substance to be detected serves as a measured variable. For this, a core of the measurement waveguide 1 embedded into a chip carries a selective layer 3 which is designed as a thin layer and which is designed for the selective accumulation of the substance to be detected. Thereby, the selective layer 3 is only deposited on an upper side of the measurement waveguide 1, so that an accumulation of the substance has a different influence on a refractive index for a TM-polarised share of the light bundle propagating in the measurement waveguide 1, than on a refractive index which differs from this, for a TE-polarised share of this light bundle.

The measurement waveguide 1 of the present embodiment example which is shown in FIG. 2 comprises a core which is embedded into the mentioned chip, wherein the chip is formed from optically single-axis lithium niobate and the core is realised by titanium diffused into this lithium niobate, this by a titanium doping. By way of this and on account of its anisotropic cross section, the measurement waveguide 1 is already double-refractive in the condition of not being occupied, wherein an optical main axis is perpendicular to a chip plane spanned by the chip and perpendicular to a longitudinal axis of the measurement waveguide, whilst a second optical main axis lies perpendicular to the longitudinal axis of the measurement waveguide 1 and parallel to the chip plane. Thus a beat length of a few 10 µm to a few 100 µm results between light shares with TE-polarisation and TM-polarisation, wherein a length of the measurement waveguide 1 which is defined by the extension of the selective layer 3 corresponds to several beat lengths.

With another embodiment shown in FIG. 3, the measurement waveguide 1 is designed as a ribbed waveguide—e.g. of silicon—and is separated from a carrier material which is not shown in FIG. 3—e.g. likewise silicon, by buffer layer which is formed for example from silicon dioxide.

In the modification, in which the sensor arrangement is to be suitable for measuring mechanical loading or if an accumulation of the substances to be detected is to cause a mechanical deformation, the measurement waveguide 1 may be designed in a free-floating manner at least in sections and be sub-etched for this, at least in locations. One may make do without the selective layer 3 if it is only mechanical loading which is to be able to be detected.

Also with a use of an optically isotropic material for the core of the measurement waveguide 1, this may have the desired characteristics if its cross section is adequately anisotropic. Thus the measurement waveguide 1 may e.g. also be formed of silicon or $Si(O)N_x$ and be e.g. designed in an extremely flat manner. By way of a mechanical biasing of the core of the measurement waveguide 1, its double-refractive characteristic may be multiplied.

The sensor arrangement of FIG. 1 comprises a light source which is not shown there, for feeding monochromatic, polarised light into the measurement waveguide 1 and which for this may comprise a polariser and may be designed and arranged such that the light which is fed into the measurement waveguide 1 has a linear polarisation which is inclined by 45° with respect to the two main axes and is illustrated in FIG. 1 by the double arrow. The light which is fed into the measurement waveguide 1 thus contains a TE-share and a TM-share of the same intensity.

The evaluation unit 2 is realised as integrated optics on a single substrate 4 which is obtained from a silicon niobate or lithium niobate wafer. The evaluation unit 2 with a first optical arm 3 and with a second optical arm 6 comprises two optical paths which in each case are formed by a single-mode waveguide and together form a Mach-Zehnder interferometer. The mentioned waveguides comprises waveguide cores which are embedded into the substrate or which are rib-like in the case of a design which is based in silicon, and these cores are separated from the substrate 34 by a buffer layer or are embedded into this. The evaluation unit 2 may e.g. be designed with SOI-technology.

The two arms 5 and 6 depart from a polarising beam splitter 7, into which the light leaving the measurement waveguide 1 is fed. With regard to the beam splitter 7, it is the case of a TE/TM splitter, so that the TM-polarised share of the light is led into the first arm 5 and the TE-polarised share is led into the second arm 6. With regard the present example, thereby the chip carrying the measurement waveguide 1 and the substrate 4 of the evaluation unit 2 are arranged in a coplanar manner.

A detailed plan view of the beam splitter 7 is shown in FIG. 4, from which one may recognise that this is realised by a directional coupler with two waveguide sections which run along a coupling section 8 parallel to one another and of which one on an upper side carries a coating 9 of gold which is shown in a hatched manner and on account of which only the TE-polarised share is coupled over into this waveguide section. Alternatively or additionally to the coating 9 of one of the waveguide sections, the two waveguide sections may also be designed with such different cross sections that the effect of a TE/TM mode splitting is achieved.

A polarisation converter 10 which is designed as a passive TE/TM mode converter is arranged within the second optical arm 6. The polarisation converter 10, of which a detail is represented in FIG. 5, is given by a waveguide which has cross-sectional shapes of the type recognisable in FIG. 5, which change along a course. By way of this, at least a part of the light transported in the second arm 6 is converted such that it obtains a TM-polarisation and by way of this may interfere with the light which is led through the first arm 5. Of course the polarisations of the mentioned shares of the light may also be exchanged. Thus also a TE-share may be led through the first arm 5 and a TM-share may be deflected into the second arm 6 which then would be converted by the polarisation converter 10 at least partly into a TE-mode.

For leading together light which is led in the two arms 5 and 6, the evaluation unit 2 comprises an optical coupler 11 which is given by a directional coupler and is designed as an optical four-point network, wherein each of two outputs of this coupler 11 is connected in each case to a light-sensitive element 12. Electrical outputs of these light-sensitive elements 12 in turn are connected to inputs of a differential amplifier 13. With this, one may determine a relative phase position between the two shares of the light which is led through the measurement waveguide 1 and the two arms 5 and 6, which depends on the measured variable, by way of evaluating an intensity distribution at the outputs of the coupler 11 forming a 3 dB-coupler.

In order to simplify this evaluation of the relative phase position, the second optical arm 6 finally also comprises a phase-shifter 14 which is arranged between the beam splitter 7 and the coupler 11 and with which the relative phase position may be changed in dependence on a control voltage which may be applied between the two electrodes, thus e.g. a shift of the relative phase position which occurs in the measurement waveguide 1 may be compensated. A phase shift is thereby effected in the phase-shifter 14 whilst utilising a dependency between the refractive index of a waveguide core of the phase-shifter 14 and an electrical field which prevails there.

In a further formation, the sensor arrangement which is schematically illustrated in FIG. 1 may also comprise several measurement waveguides 1 which are optically connected to the input of the beam splitter 7 or, e.g. by way of optical switches, may be selectively connected to this and may be read out one after the other by way of this. A sensor part which contains one or more such measurement waveguides 1, may be manufactured also as an array in an inexpensive manner, e.g. with CMOS-technology which is known per se or with lithium niobate technology.

A sensitivity of the suggested system may be adapted to different measurement tasks by way of a suitable preselection of a sensor length, thus of a length of the measurement waveguide 1, and a number of TE/TM beat lengths which results with this. The same applies to the application of selective thin layers which are to be selected accordingly and are known from the state of the art, on the measurement waveguide 1.

For detecting the substance—for example in the mentioned modification for detecting the loading—with the described arrangement, thus the light with the two shares of different polarisation is fed into the measurement waveguides 1 which for this polarisation displays a double refraction which changes depending on the measured variable. After leaving the measurement waveguide 1, the two shares are separated and are led through the two different optical arms 5 and 6. The polarisation of the share which is led through the second arm 6 is changed with the polarisation converter 14 such that light with components of the same polarisation exits at an output of this arm 6 and of the other arm 5. The two shares are superimposed by way of a coupler 11 at the output of the two arms 5 and 6, whereupon one may detect a phase shift which has occurred in the measurement waveguide 1 by way of intensity measurement of a superposition of the two shares—thus a shift of a relative phase position between the two shares—from which one may deduce the measured variable.

What is claimed is:

1. An optical sensor arrangement, comprising:
   a measurement waveguide configured to display a double refraction which changes depending on a measured variable; and
   an optical evaluation unit, comprising:
      two optical arms comprising waveguides and forming a Mach-Zehnder interferometer;
      an optical coupler configured to lead together light which is led in the two optical arms, at least one output of the optical coupler is optically connected to at least one light-sensitive element; and
      a polarizing beam splitter from which the two optical arms depart, the polarizing beam splitter configured to provide respective light components, having different polarizations, respectively to the two optical arms;
   wherein the measurement waveguide is connected in front of an optical input of the polarizing beam splitter; and
   wherein a polarization converter is arranged in a course of one of the two optical arms.

2. The optical sensor arrangement according to claim 1, wherein the beam splitter is arranged on a common planar substrate with the optical coupler and with the optical arm that has the polarization converter.

3. The optical sensor arrangement according to claim 1, wherein the measurement waveguide carries a selective layer for the accumulation of a substance to be detected.

4. The optical sensor arrangement according to claim 1, wherein the measurement waveguide includes at least one free-floating section configured to detect mechanical loading.

5. The optical sensor arrangement according to claim 1, wherein a core of the measurement waveguide includes a material having a single optical axis and/or having an anisotropic cross section.

6. The optical sensor arrangement according to claim 1, wherein the measurement waveguide is double-refractive in a non-loaded and/or non-occupied condition and has a length which corresponds to several beat lengths between light components of different polarizations.

7. The optical sensor arrangement according to claim 1, further comprising a light source for feeding polarized light into the measurement waveguide, the light source configured such that the light fed into the measurement waveguide contains light components of two polarizations which are so different that in each case one of the light components is led into each of the two optical arms of the evaluation unit by the beam splitter.

8. The optical sensor arrangement according to claim 1, wherein the measurement waveguide and/or the waveguides forming the two optical arms of the evaluation unit include single-mode waveguides.

9. The optical sensor arrangement according to claim 1, wherein at least one of the two optical arms comprises a phase-shifter.

10. The optical sensor arrangement according to claim 1, wherein the polarizing beam splitter includes a directional coupler with waveguide sections running parallel to one another along a coupling section and having different cross sections and/or wherein at least one of the waveguide sections carries a metallic coating.

11. The optical sensor arrangement according to claim 1, wherein the optical coupler is given by an optical four-point network, wherein each of two outputs of the optical coupler is connected to a light-sensitive element.

12. The optical sensor arrangement according to claim 1, wherein the polarization converter includes a passive polarization converter.

13. The optical sensor arrangement according to claim 1, further comprising several measurement waveguides selectively optically connected to an input of the polarizing beam splitter.

14. A method for detecting a substance and/or a mechanical load, comprising:
   feeding light having light components with two different polarizations into a measurement waveguide;
   displaying, using the waveguide, a double refraction depending on an accumulation of a substance and/or a mechanical load;
   separating the light components, using a polarizing beam splitter, after the light components leave the measurement waveguide;
   changing the polarization of at least one of the light components as the light components are respectively led through two different optical arms;
   superimposing the two light components at an output of the two arms; and
   detecting a phase shift between the two light components using an intensity measurement of a superposition of the two light components.

* * * * *

UNITED STATES PATENT AND TRADEMARK OFFICE
CERTIFICATE OF CORRECTION

PATENT NO. : 8,665,448 B2  Page 1 of 1
APPLICATION NO. : 13/202206
DATED : March 4, 2014
INVENTOR(S) : Heidrich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 58 days.

Signed and Sealed this
Twenty-ninth Day of September, 2015

Michelle K. Lee
*Director of the United States Patent and Trademark Office*